(12) United States Patent
Lin et al.

(10) Patent No.: US 6,436,709 B1
(45) Date of Patent: Aug. 20, 2002

(54) LOW PRESSURE-ACCELERATED PARTICLE GENE GUN

(75) Inventors: Hao-Jan Lin, Taipei; Ker-Jer Huang, Taoyuan Hsien; Horng-Tsann Yang, Taoyuan; Wen-Chung Chen, Taotuan Hsien, all of (TW)

(73) Assignee: Bioware Technology Co., Ltd., Taipei Hsien (TW)

( * ) Notice: Subject to any disclaimer, the term of this patent is extended or adjusted under 35 U.S.C. 154(b) by 0 days.

(21) Appl. No.: 09/990,981

(22) Filed: Nov. 21, 2001

(30) Foreign Application Priority Data

Oct. 19, 2001 (TW) ........................................ 90125886 A

(51) Int. Cl.$^7$ ............................................... C12N 15/64
(52) U.S. Cl. ..................... 435/459; 435/470; 435/285.3
(58) Field of Search .................................. 435/459, 470, 435/285.3

(56) References Cited

U.S. PATENT DOCUMENTS 6,004,287 A * 12/1999 Loomis et al. ................. 604/68

* cited by examiner

Primary Examiner—James Ketter
(74) Attorney, Agent, or Firm—J.C. Patents

(57) ABSTRACT

A gene gun is described wherein the contour design of the spray nozzle of the gene gun modifies the operation of the gene gun. A low pressure gas is used to accelerate the micro-particles that are coated with nucleic acid of a foreign gene into cytoplasma or nuclei of an animal or plant cell to express the special protein and to generate the new biological function.

22 Claims, 7 Drawing Sheets

LOW PRESSURE-ACCELERATED PARTICLE GENE GUN

CROSS-REFERENCE TO RELATED APPLICATION

This application claims the priority benefit of Taiwan application Ser. no. 90125886, filed on Oct. 19, 2001.

BACKGROUND OF THE INVENTION

1. Field of Invention

The present invention relates to a structure of a gene gun. More particularly, the present invention relates to the contour design of the spray nozzle of the gene gun, which would modify the gene gun operation, wherein gene transformation is accomplished with nitrogen gas and only low pressure, obviating damages to cells and the problem of noise.

2. Description of Related Art

Gene delivery system has been widely used in gene therapy and optimizing the genetic make-up in plant material. The current gene transformation method includes using a physical method for gene transformation, such as the development by Klein (1987) for more than ten years on particle gun and its application in gene transfer and gene transformation. The technique of particle gun is first applied in the research and development of plant materials since this technique can effectively overcome the barrier of plant cell wall. Particle gun is also applicable to the research and development of other fields, for example, gene therapy of mammalian cells and hormone cells, and the recently developed DNA vaccination.

The earlier devised particle gun system uses a gas to pressurize a gas acceleration tube. When a preset high pressure is reached in the pressurized chamber, a DNA/RNA particle-coated thin film is accelerated by a resulting shock wave into a stopping screen. The DNA/RNA particles continue to accelerate to enter the target tissue due to the inertia effect. The gas that is used to create the high pressure in the pressurized chamber varies and is normally maintained at a pressure of about 1000 lb/sq. in. (PSI).

The particle gun technique has improved tremendously in the recent years. The DNA/RNA-coated microcarriers are coated on the inside wall of a sample cartridge. The microcarriers accelerate for maximum penetration into the target based on the high pressure shock wave principle (Henning et al., 1999). A major disadvantage of the aforementioned methods is the loud noise resulting from the shock wave. The high speed and high pressure gas that is generated by the shock wave also causes cell deaths. Moreover, the gas used in the conventional particle gun technique employs the expensive helium gas.

SUMMARY OF THE INVENTION

According to the theory of aerodynamic, a supersonic flow is generated when the pressure difference between the inside and the outside pressures of the nozzle is greater than 1.9 atm. Further based on the bi-phase flow theory, a high speed air flow can carry the particles that are few centimeters apart in the air from a stationary state to accelerate to an extreme high speed. Based on these two theories, the present invention provides a low-pressure gene gun, wherein the problems of low noise, cell death induced by shock wave and the application of the expensive helium gas are prevented.

To resolve the aforementioned problems, the present invention provides a gene gun, which is operable under a low pressure, using a nitrogen gas or a helium gas to directly accelerate the micro-carriers, such as gold or tungsten particles, to an extreme high speed, for example, greater than 200 m/sec. The micro-carriers, on which the surface is coated with nucleic acid of a foreign gene, penetrate through the cell membrane of animal or plant epidermal cells and enter into cytoplasma or the cell nucleus to express the special protein and to generate the new biological function.

The present invention provides a gene gun, wherein the gene gun is applicable in gene transformation. According to a preferred embodiment of the present invention, the contour design of the spray nozzle of the gene gun allows a modification of the gene gun operation to operate at a much lower pressure. A gas travelling at supersonic speed is used to accelerate the micro-carrier from a stationary state to an extreme high speed, penetrating the epidermis and entering the cell.

Since a low pressure is used, particles are driven into the cell to achieve gene transformation with minimal noise and damages to the cells. Moreover, the conventional gene gun requires a helium gas source, whereas a nitrogen gas is also acceptable for the present invention. Depending on the situation, a selection between a nitrogen gas source and a helium gas source is provided by the present invention.

It is to be understood that both the foregoing general description and the following detailed description are exemplary, and are intended to provide further explanation of the invention as claimed.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee. The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figure 1:
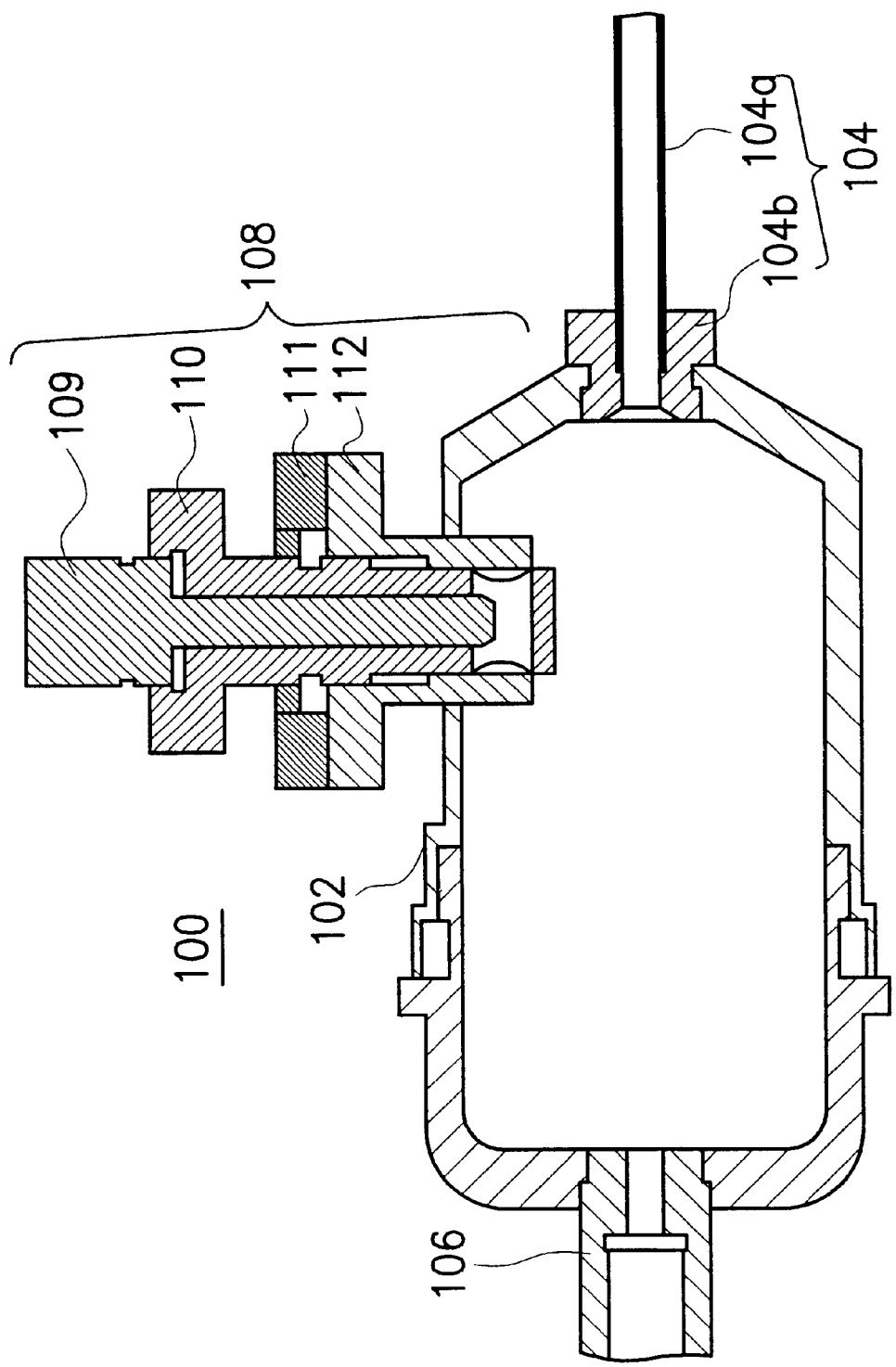
FIG. 1 is a cross-sectional view of a gene gun according to a preferred embodiment of the present invention.

Referring to FIG. 1, FIG. 1 is across-sectional view of a gene gun 100 according to a preferred embodiment of the present invention. The gene gun 100 of the present invention is divided into four parts, comprising at least a pressurized chamber 102, a sprayer 104, a backside connector 106 and a material delivery system 108. A gas is delivered from the backside connector 106 to the pressurized chamber 102 via tubing (not shown in Figure). As the gas in the pressurized chamber 102 is built up to a preset pressure, the high-pressure gas and the micro-particles carried by the high-pressure gas are sprayed out through the sprayer 104.

Figure 3:
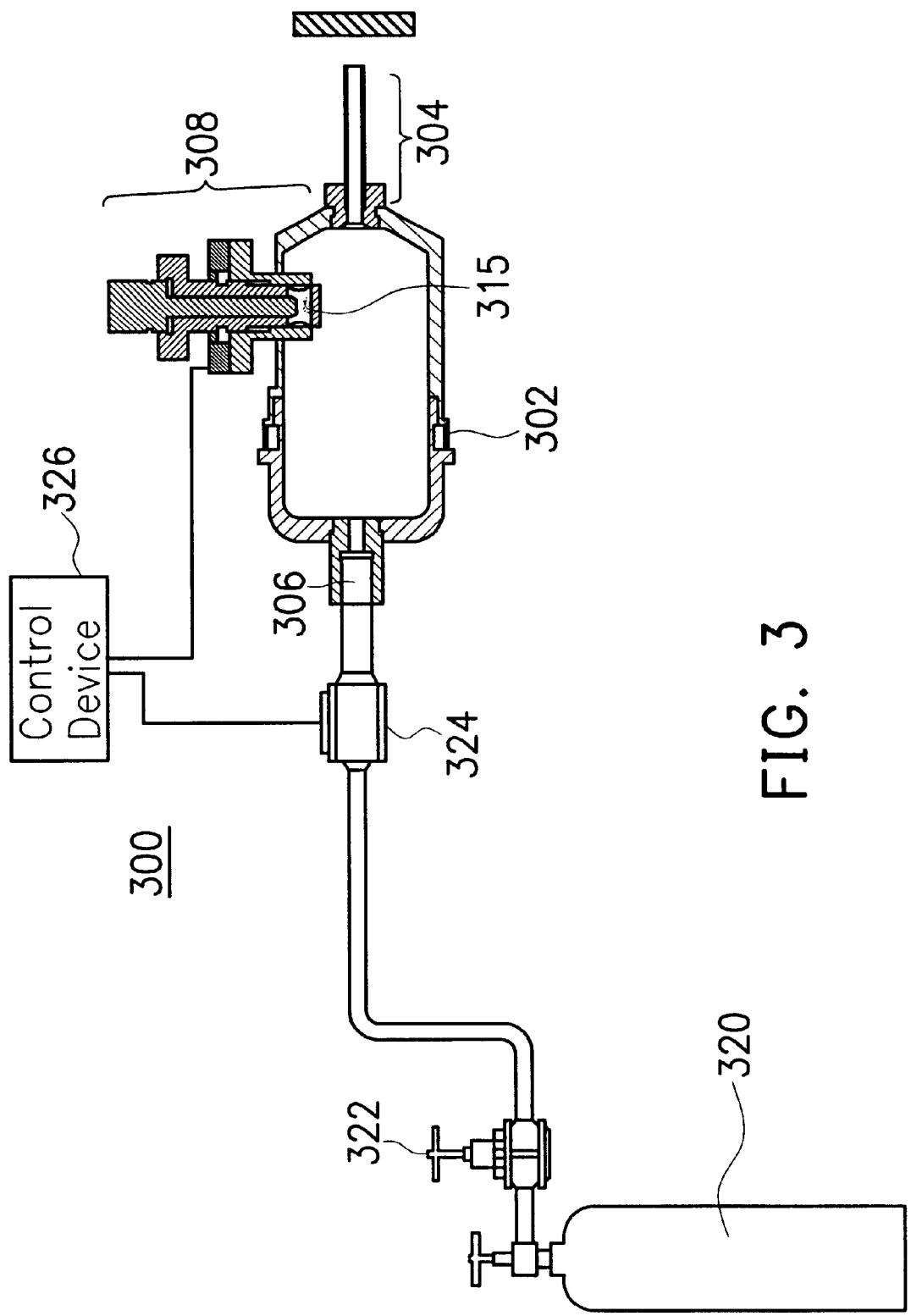
FIG. 3 illustrates the connection between the gene gun and tube assembly.

The basic structure of the gene gun of the present invention further includes a handle structure (not shown in Figure). The handle structure is connected to a triggering device (not shown in Figure). As the micro-particles are ready to be discharged, a control device (as shown in FIG. 3) is initiated. A gas is then delivered into the pressurized chamber while the delivery of micro-particles into the pressurized chamber from the material delivery system is also initiated. The handle structure and the triggering device are not limited to any single type of technology or assembly. Any existing assembly or technology for the handle structure or the triggering device can be used. Since the handle structure and the triggering device are not the essential features of the present invention, details for the handle structure and the triggering device will not be reiterated.

In general, the micro-particles are accelerated by a gas to a velocity of about 200 to 300 meter/sec, and this speed does not exceed the speed of sound. The sprayer 104, as shown in FIG. 1, includes at least a terminal spray tube 104*a* and a nozzle 104*b*. According to the theory of aerodynamics, as the pressure difference between the internal and the external of the spray nozzle is greater than 0.9 atm, a supersonic flow is generated. If the cross-sectional diameter of the nozzle converges initially and then diverges to a small degree, a supersonic flow is generated in the nozzle 104*b*. The gas velocity gradually decreases as the gas enters the spray tube 104*a*. Increasing the length of the spray tube 104*a*, the gas velocity decreases. The gas velocity can thereby be controlled within a certain limits according to the length of the spray tube 104*a*.

The gene gun of the present invention can target a different type of cell with a different particle speed by adapting the following mechanisms:

(1) a different gas speed (2) a different length of the terminal spray tube (3) a different gas According to one preferred embodiment of the present invention, a special spray nozzle is employed. In accordance of this special spray nozzle, a different particle speed is achieved by varying the length of the terminal spray tube and the type of gas source. It is intended that the specification and examples to be considered as exemplary only. Additional advantages and modifications are readily occurred to those skilled in the art from the consideration of the specification and the practice of the invention disclosed herein.

According to a preferred embodiment of the present invention, an appropriate design includes an application of ethanol suspension or dry powdery micro-particles and a material delivery system as disclosed in the present invention. The micro-particles can uniformly accelerate to a required velocity without the application of high pressure, while the damage to the target cells is mitigated. Moreover, the contour design of the spray nozzle 104*b* and the spray tube 104*a* allows the pressure at the exit of the spray nozzle to approach the atmospheric pressure. Damages to the target cells are thereby reduced.

Figure 2:
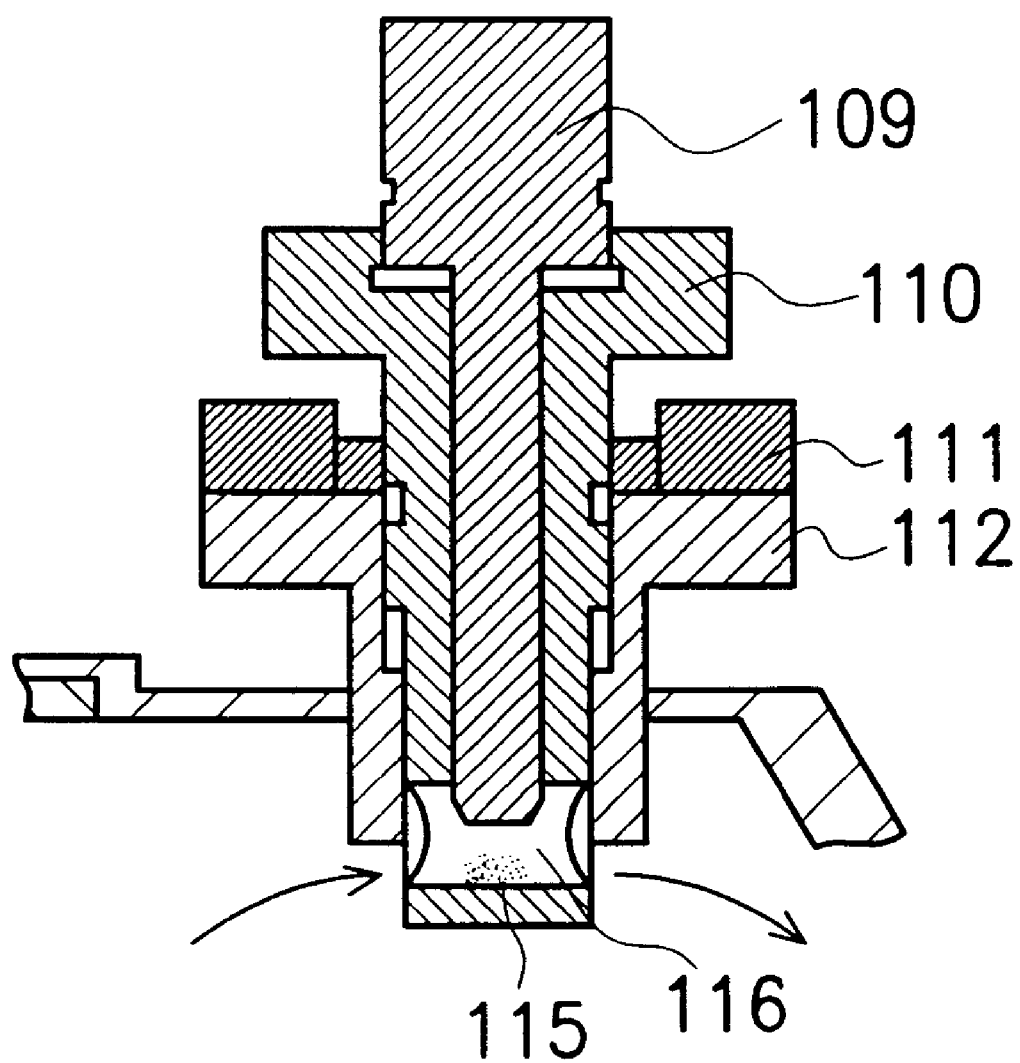
FIG. 2 is a cross-sectional view of a material delivery system illustrating the micro-particles being carried into the pressurized chamber by the high-speed air flow when the material delivery system is operating.

The material delivery system 108, as illustrated in FIG. 2, comprises at least four parts: a feeding tube sealer 109, a feeding tube 110, a clutch 111 and a feeding tube sleeve 112. The feeding tube sleeve 112 is connected to the pressurized chamber with screws or by welding. The clutch 111, for example, an electromagnetic clutch, is fixed onto the feeding tube sleeve 112 with glue or screws. The feeding tube 110 is placed in the central open space of the feeding tube sleeve 112 and the electromagnetic clutch 111. The micro-particles 15 are placed onto the particle loading station 116 at the bottom end of the feeding tube 110. The feeding tube sealer 109 is placed in the central open space of the feed tube 110, sealing the feeding tube 100. The material delivery system 108 further includes an o-ring (not shown in Figure) to air-sealed the feeding tube 110 in the feeding tube sleeve 112 and the clutch 111.

Normally, the material delivery system 108 is closed. As the micro-particles are set to deliver, the feeding tube sealer 109 is lifted. The micro-particles are then poured into the feeding tube 110 onto the particle loading station 116. As the micro-particles are ready to be discharged, an electrical current is sent to the electromagnetic clutch 111, causing both the electromagnetic clutch 111 and the material delivery system 108 to move a short distance in a downward direction. As shown in FIG. 2, these micro-particles 115 are exposed to the high-velocity gas flow (as indicated by the arrows in FIG. 2). The high-velocity gas flow would enter the feeding tube 110 through the small opening (now shown in Figure) on the feeding tube 110 and carry the micro-particles 115 out of the feeding tube 110. The micro-particles 115 are further accelerated to the required velocity by the sprayer 104. The feeding tube 110 can also manually move a short distance in a downward direction before the influx of the high velocity gas flow.

According to the preferred embodiment of the present invention, the micro-particles are coated with nucleic acid type of material. The micro-particles include gold and tungsten and the nucleic acid type of material includes DNA or RNA. The diameter of the micro-particles is preferably from 0.6–1.5 $\mu$m. The micro-particles are preferably in an ethanol suspension type or dry powdery form.

FIG. 3 illustrates the entire gene gun system. The gas source for the gene gun system 300 is provided from a gas tank 320. The gas source from the gas tank 320 includes a helium gas, a nitrogen gas or other type of gas. The helium gas can travel at velocity greater than 1000 m/s. Moreover, less damage is inflicted upon the target cell because the mass of helium is lower. Helium is thus an ideal gas, except for being too expensive. Using helium gas is essential on animal or plant cells with a thicker keratin or wax layer. However, using a nitrogen gas for the gene gun is sufficient for the easily penetrated biological system. The gas in the gas tank 320 is set at a certain pressure by a pressure regulator 322. The pressure in the pressurized tank of the gene gun has to be greater than 1.9 atm. Due to the drop of the gas pressure in the tubing, the pressure regulator 322 has to set at a higher pressure. The preferred range of pressure will be 4.0–8.0 atm.

As shown in FIG. 3, the gas is passed from the gas tank 320 through the pressure regulator 322 and the tubing. A control valve 324 is further used to determine whether the gas would enter the pressurized chamber 302 through the back-side connector 306. The control valve 324 is controlled by a controller 326. When the gene gun system 300 is operating, the pressure regulator 322 is set at an appropriate pressure. The RNA or DNA-coated particle powders are placed in the feeding tube 110 (as shown in FIG. 2) of the material delivery system 308. The trigger device that is connected to the handle structure of the gene gun system (Figure not shown) is initiated, the control device 326 is set off, sending a signal to open the control valve 324. The material delivery system 308, on the other hand, remains shut to provide a sufficient time to establish a flow field and to remove other irrelevant gases and materials from the pressurized chamber 102 (as shown in FIG. 1). After the establishment of the fluid flow field, another signal is sent from the control device 326 to the electromagnetic clutch 111 (as shown in FIG. 2) in the material delivery system 308. The electromagnetic clutch 111 is released, pushing the feeding tube down to expose the sidewall of the feeding tube 110, wherein openings or opening-like structures are revealed on the sidewall of the feeding tube 110. The micro-particles 315 in the particle loading station 116 (as shown in FIG. 2) of the feeding tube 110 are then carried out by the high-velocity gas flow and are discharged into the target tissue through the sprayer 304.

If the micro-particles are in suspension, according to another preferred embodiment of the present invention, a gravity dispensing mechanism is employed to release a suspension droplet of the micro-particles from the material delivery system. The micro-particles droplet is then carried away by the high velocity gas flow and is discharged at a high speed into the target tissue.

Figure 4:
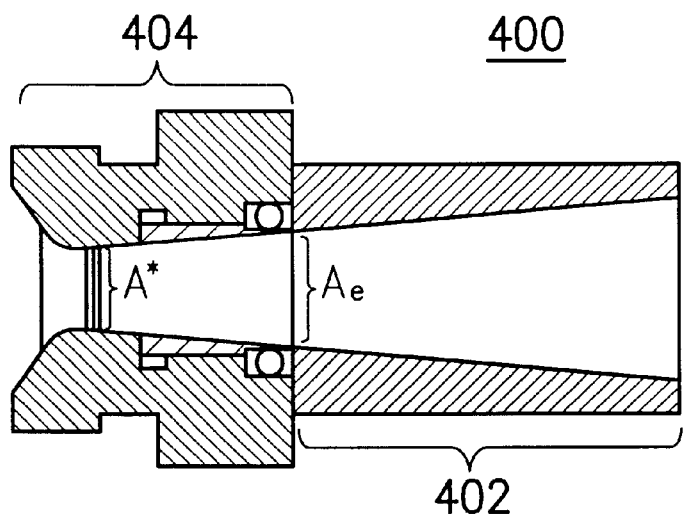
FIG. 4 is a cross-section view of a sprayer according to a preferred embodiment of the present invention.

In order for the micro-particles to travel at a high speed, the present invention provides a high-speed sprayer 400, as shown in FIG. 4. Unlike the conventional straight spray tube, the spray tube 402 of the present invention is conical shape, allowing the speed of the gas flow to achieve the supersonic flow rate and the speed of the micro-particles to approach the speed of sound. The spray nozzle 404 comprises a contour entrance, allowing the discharged micro-particles to be more evenly distributed and are not localized at the exit, which causes cell death. Moreover, the gas pressure at the exit of the spray nozzle approaches atmospheric pressure to mitigate damages to the cell.

The spray tube and the spray nozzle of the present invention are designed according to the following theory: Assuming the flow field is an isentropic flow, the ratio of the area of the spray nozzle (Ae) and the area of the spray neck A* is $$\frac{Ae}{A^*} = \frac{1}{Me}\left[\frac{2}{\gamma+1}\left(1+\frac{\gamma-1}{2}Me^2\right)\right]^{\frac{\gamma+1}{2(\gamma-1)}}$$

wherein, Me is the Mach number, which is a ratio of the gas flow rate over the speed of sound and $\gamma$ is the specific heat ratio. If Me, Ae and $\gamma$ are defined, A* is determined.

Similarly, if the pressure at the exit of the spray nozzle, the pressure in the pressurized chamber Po can also be determined according to the following equation $$Po = P\left(1+\frac{\gamma-1}{2}Me^2\right)^{\frac{\gamma}{\gamma-1}}.$$

If the pressure in the pressurized chamber is the gas tank pressure, the required pressure in the gas tank Pc is determined according to the following equation $$Pc = P\left(1+\frac{\gamma-1}{2}M_{in}^2\right)^{\frac{\gamma}{\gamma-1}}\frac{1}{Ld}$$

wherein Ld is dump loss.

Since a certain gas flow rate is needed to carry out the micro-particles in the feeding tube, the necessary gas tank pressure is resulted by defining the Mack number at the entrance of the pressurized chamber ($M_{in}$).

Moreover, under the steady state condition, the mass flow rate in $\dot{m}_{in}$ is equal to the mass flow rate out $\dot{m}_{out}$, $$\dot{m}_{in} = (\rho A V)_{out}$$

$$A_{in}\frac{P_c}{\sqrt{T_o}}\sqrt{\frac{\gamma}{R}}\frac{M_{in}}{\left(1+\frac{\gamma-1}{2}M_{in}^2\right)^{\frac{\gamma+1}{2(\gamma-1)}}} = A^*\frac{P_0}{\sqrt{T_0}}\sqrt{\frac{\gamma}{R}}\sqrt{\left(\frac{2}{\gamma+1}\right)^{\frac{\gamma+1}{\gamma-1}}}$$

wherein $\rho$ is the gas density, To is the temperature in the pressurized chamber, $A_{in}$ which is area of the entrance of the pressurized chamber from the gas tank. $A_{in}$ is thereby easily determined.

Figure 5:
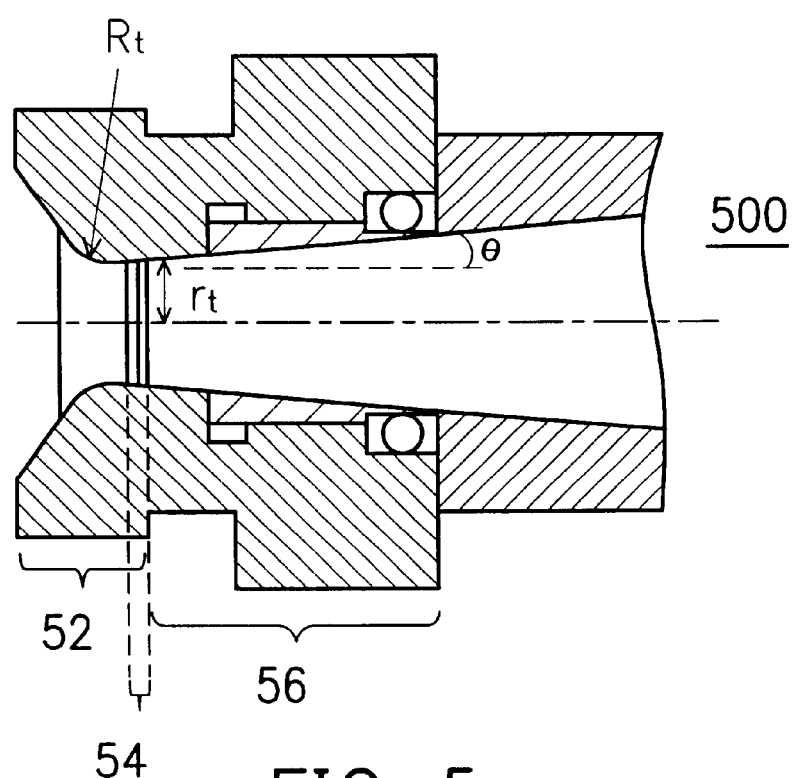
FIG. 5 is a cross-sectional view of a spray nozzle according to a preferred embodiment of the present invention.

FIG. 5 illustrates the contour design of the spray nozzle 50 of the present invention. The spray nozzle 50 is designed to comprise a converging part 52 and a diverging part 56. The transition region between the converging part 52 and the diverging part 56 is the spray neck 54. The contour of the spray nozzle 50 is obviated from any abrupt transition to allow a smooth gas flow. A general rule for designing the spray nozzle 50 of the present invention is as follow:

(1) the simplified design, wherein the gas flow rate exiting the spray nozzle is not uniform.

As shown in FIG. 5, $R_t$ represents the curvature radius of the converging part 52 and $r_t$ is the radius of the spray neck 54, wherein $r_t<R_t<2r_t$ for the converging part of the simplified design. $\ominus$, as shown in FIG. 5, is the angle between the diverging part 56 and center axis of the spray nozzle and the spray tube (broken lines), wherein $\ominus$ is less than 15 degrees for the converging part of the simplified design. The contour of the converging part of the spray nozzle, is a diverging straight tube, forming a coned shape structure. The angle $\ominus$ between the slanted straight line and the center axis is less than 15 degrees, and is preferably between 10 to 15 degrees.

(2) the uniform gas flow rate design.

The direction of the gas flow, at the spray nozzle, is not parallel to the center axis. In order to provide a gas flow that parallels to the center axis, the expansion wave generated in the spray neck of the above simple design of the diverging part must be compensated by a special curvature design of the spray nozzle.

Since the gas flow rate achieves supersonic at the exit of the spray nozzle, a coned shape spray tube or a straight spray tube is connected to the spray nozzle to accelerate the micro-particles to high a speed, which is proven to be effective in penetrating into the epidermal cell, through the cell wall and the cell membrane.

Particle Coating Treatment

Tungsten micro-carriers are coated with plasmid DNA following a modified Birch's protocol (details can be referred to /botany.uq.edu.au/research/plant biotech/). A 50 mg of microcarriers is suspended in 1 ml of 50% glycerol and autoclaved. 50 ml of the suspension is used per set of particle preparation (5 shots). The suspension is centrifuged briefly and the supernatant is discarded and is re-suspended in 1 ml of sterile distilled water. The re-suspended micro-carriers is then vortexed at low speed. During the vortexing, 100 µl of DNA (1.0 µg/µl), 100 µl 0.5 M CaCl2 (MERCK 1.02382), and 100 µl of 0.05 M spermidine (SIGMA -0266) are added. The vortexing speed is increased and continued for another 3 minutes. The mixture is briefly centrifuged at 10,000 rpm and the supernatant is discarded. Tungsten particles are centrifuged and re-suspended by washing with absolute ethanol for three times and are placed under vacuum to dry out.

Injection of Particles 1 mg of DNA-coated particle in ethanol suspension or dry-out powder (avoid to over-dry) is loaded onto the particle-loading station in the front pressurized chamber. Nitrogen pressure of about 50–100 psi is used in a target distance of 5–25 cm of shooting.

Transient expression results in onion (Allium Cepa) epidermal cells

The β-glucuronidase (GUS) gene in the pBI121 vector (CLONTECH) was used as the reporter gene in our transient expression assay. Expression of the fusion gene was driven by the cauliflower mosaic virus 35S promoter. Plasmid DNA coated onto 1.1 micron tungsten (Grade M-17, Bio-Rad #1652267) was introduced into onion epidermal cells. After the injection of particles, the onion peels were incubated in 100% relative humidity moist chamber for 16 hrs at room temperature. The GUS activity in the cells was detected as blue color precipitates by incubating the onion peels in a staining solution (100 mM sodium phosphate, pH 7.0, 10 mM EDTA, 0.5 mN ferricyanide, 0.5 mM ferrocyanide and 1 mM 5-bromo-4-chloro-3-indolyl β-D-glucuronic acid overnight at 37° C.

Figure 6:
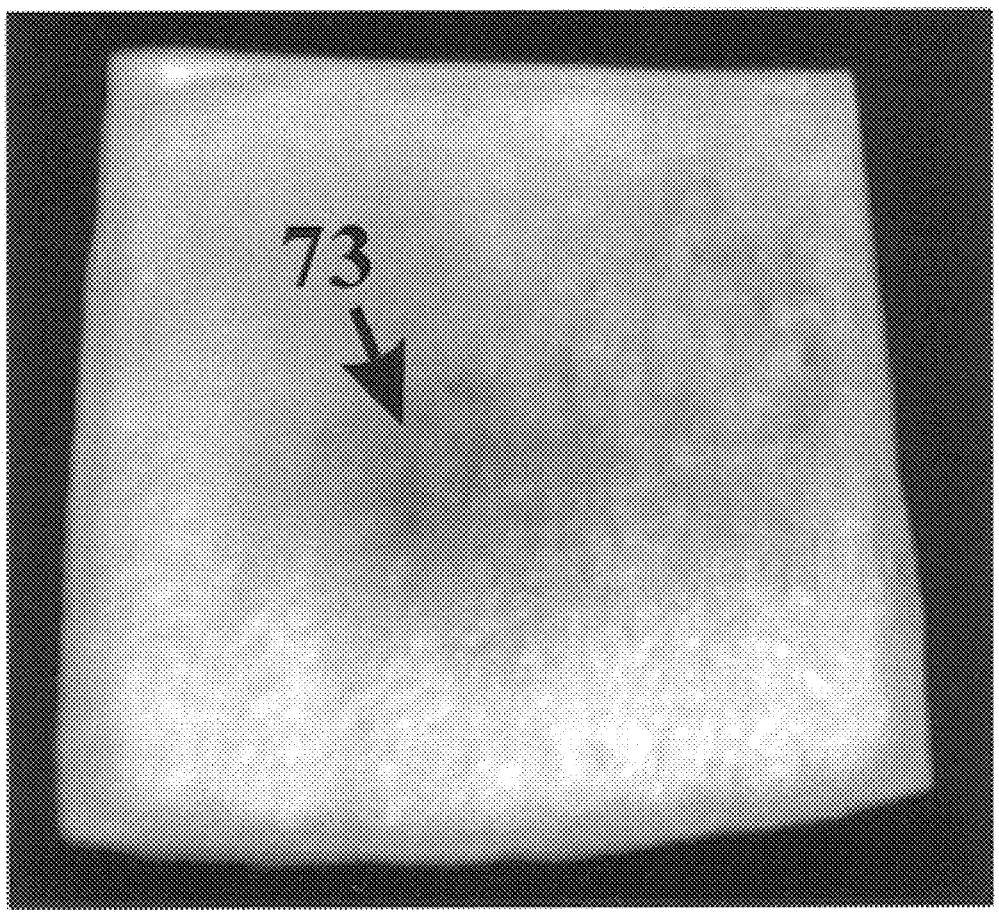
FIG. 6 is the transient expression results in onion epidermal cells.
Figure 7:
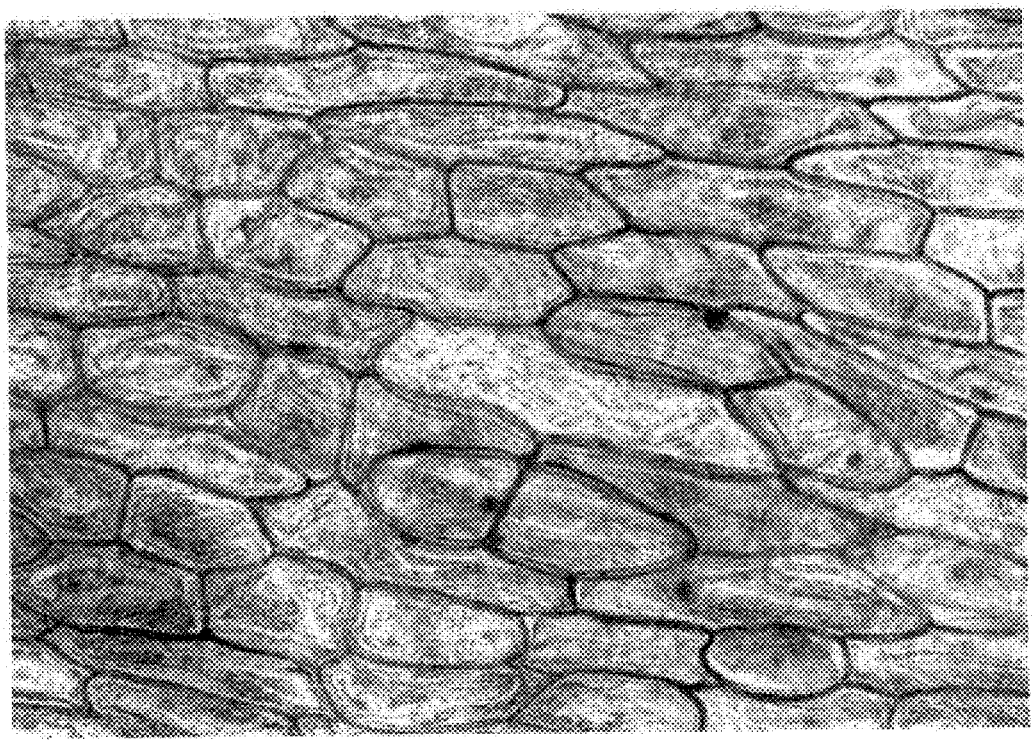
FIG. 7 is a magnified view of onion epidermis cells expressing GUS activity. The bombarded tissues were incubated in 100% alcohol and photographed 7 days after the treatment for GUS assay.

Experimental result indicates that, as clearly shown in FIG. 6, blue sentiments are present near the injection site of the tungsten micro-carriers 73. The result indicates that using the gene gun of the present invention, the GUS gene is successfully transferred into the onion cell. FIG. 7 is the magnified view of onion epidermal cells expressing GUS activity. The bombarded tissues were incubated in 100% alcohol and photographed 7 days after the treatment for GUS assay. Blue sentiments are clearly present in onion epidermal cells bombarded by tungsten miro-carriers. The success rate in gene transfer is higher than 95%. Based on these results, the GUS gene is successfully transferred into the onion cell without inducing damages to the cell structure Gene Gun Experiment Performed on Mice Particle Coating Treatment A 5 mg of gold micro-carriers (with size of about 1.5 to 3 micron) is added to 20 µl of plasmid (1 µg/µl) (CLONTECH, pEGFPN2) and is vortexed for a few seconds. During the vortexing, 20 µl of the 0.5M CaCl$_2$ and 20 µl 0.05M spermidine is added. The evenly mixed solution is then placed on ice for about 10 minutes, followed by centrifuging at 12000 rpm for 30 seconds. The supernatant is discarded and the gold micro-particles are re-suspended by washing with 200 µl of absolute ethanol. The above procedures are repeated twice, which include washing the micro-particles with absolute ethanol for three times. The micro-particles are subsequently suspended in 100 µl of absolute alcohol and 10 µl of the suspension is used each time.

Specimen

Figure 8:
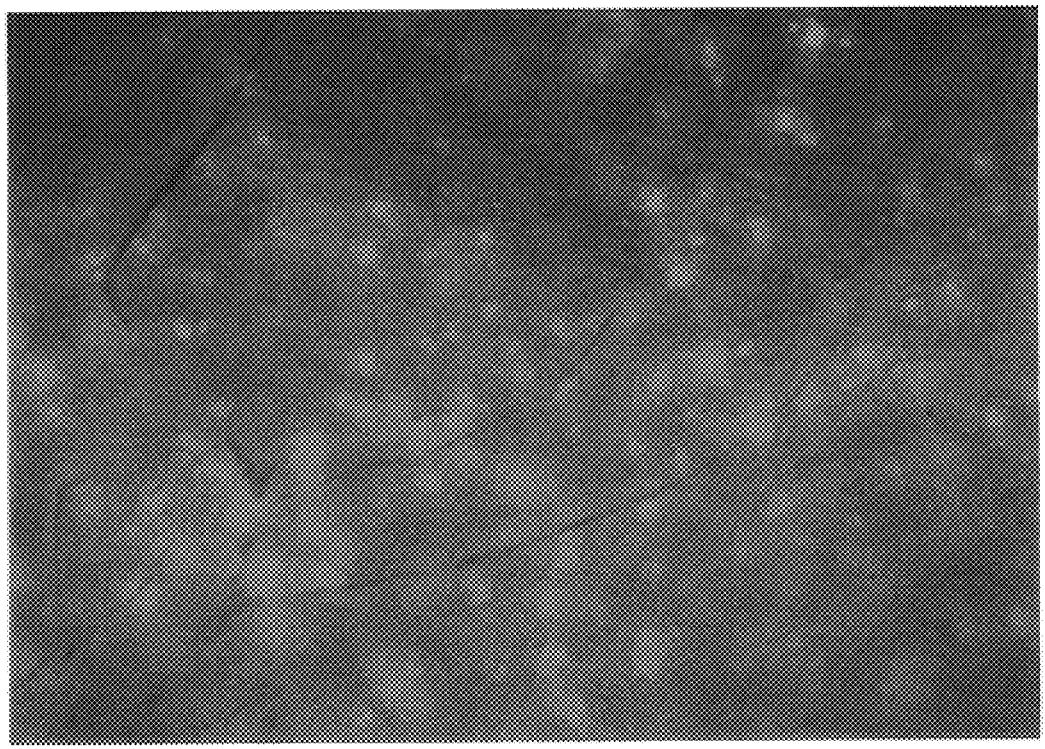
FIG. 8 is a magnified view of the abdomen epidermal cells of a mouse subsequent to particles bombardment using the gene gun of the present invention. EPFG fluorescence light is clearly present in the cells.

The specimen used for the gene gun experiment is BALB/c mice of about 8 to 9 weeks old. Hair at the abdomen of the mouse is shaved to expose the skin of the mouse Injection of Particles A 10 µl of the micro-particles suspension is loaded into the gene gun of the present invention. The bombardment condition includes 100 psi of nitrogen gas at a distance of about 05 to 1 cm. The target of bombardment is the abdomen of the mouse. The mouse is not anesthetized. Three days after the bombardment treatment, the mouse is sacrificed, The skin of the mouse abdomen is removed and examined under an Olympus 1×70 microscope using an absorption wavelength of 483 nm and an exciting wavelength of 503 nm. FIG. 8 is a magnified view of the abdomen epidermal cells of a mouse subsequent to particle bombardment using the gene gun of the present invention. As shown in FIG. 8, EGFP fluorescence light is clearly present in the abdomen epidermal cells of the mouse after being bombarded by micro-particles.

Accordingly, the micro-carriers can be delivered quietly and at an extremely high speed at a lower pressure. The gene-coated micro-particles thus acquire a sufficient momentum to penetrate through the epidermal cell wall and enter into the cell to transform the cells.

Moreover, due to the contour design of the spray nozzle, the operation of the gene gun is modified to allow an even distribution of the gene-coated micro-particles. Since the pressure at the nozzle opening is close to atmospheric pressure, the target cell is prevented from being damaged.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A low pressure-accelerated particle gene gun, comprising:
    a gas source to provide a gas;
    a gas pipe with a first end of the gas pipe connected to the gas source and a second end of the gas pipe connected to a valve, wherein an opening and an closing of the valve is controlled by a control device to control a delivery of the gas;
    a gene gun apparatus, the gene gun apparatus comprises at least:
        a handle structure connected a triggering device, wherein the triggering device is connected to the control device;
        a pressurized chamber connected to the handle structure, wherein the pressurized chamber comprises a front-side and a back-side;
        a sprayer, the sprayer includes a spray nozzle and a spray tube, and the spray nozzle comprises a front part and a back part, the front part of the spray nozzle is connected to the spray tube and the back part of the spray nozzle is connected to the back-side of the pressurized chamber, the spray nozzle comprises an interior contour, wherein the interior contour of the spray nozzle comprises a diverging part and a converging part;
        a connector, a first end of the connector is connected to the front-side of the pressurized chamber and a second end of the connector is connected to the valve, wherein the gas is flow from the valve to enter into the pressurized chamber; and
        a material delivery system connected to a top part of the pressurized chamber, wherein the material delivery system comprises at least a feeding tube sealer;

a feeding tube, a clutch, and a feeding tube sleeve, the feeding tube sleeve is firmly attached to the pressurized chamber with the clutch connected to a top of the feeding tube sleeve, the feeding tube is placed in a center open space of the feeding tube sleeve and the clutch and the feeding tube comprises a particle loading station wherein micro-particles are placed, and a feeding tube sealer is placed in the center open space of the feeding tube to seal the feeding tube, wherein the control device is connected to the clutch to control an initiation of the clutch to release the micro-particles, allowing the micro-particles to be carried away by a high speed gas flow in the pressurized chamber and sprayed from the sprayer.

2. The low pressure-accelerated particle gene gun of claim 1, wherein the spray tube is a diverging straight tube.

3. The low pressure-accelerated particle gene gun of claim 1, wherein the spray nozzle further comprises a spray neck positioned between the diverging part and the converging part, and a range of the interior contour of the converging part includes: $r_t<R_t<2r_t$, wherein $R_t$ represents a curvature radius of the converging part, $r_t$ is a radius of the spray neck.

4. The low pressure-accelerated particle gene gun of claim 1, wherein $\ominus<15$ degrees, wherein $\ominus$ is an angle between the diverging part and the center axis.

5. The low pressure-accelerated particle gene gun of claim 1, wherein the micro-particles include a plurality of nucleic acid coated tungsten particles.

6. The low pressure-accelerated particle gene gun of claim 1, wherein the micro-particles include a plurality of nucleic acid coated gold particles.

7. The low pressure-accelerated particle gene gun of claim 1, wherein the micro-particles are in a suspension or dry powdery micro-particles.

8. The gene gun of claim 1, wherein an O-ring is further included to air-seal the feeding tube in the center air space of the feeding tube sleeve and the clutch.

9. The gene gun of claim 1, wherein the gas includes a nitrogen or a helium gas.

10. A low pressure-accelerated particle gene gun, comprising:

a gas supply mechanism to provide a gas;

a connection mechanism, the connection mechanism connects the gas supply mechanism to a pressurized chamber and a gas is flow into the pressurized chamber through the connection mechanism, wherein the pressurized chamber comprises a chamber front-side and a chamber back-side, a control device, the control device is connected to the connection mechanism and controls an opening of the connection mechanism to control a supply of the gas;

a sprayer, the sprayer comprises a spray nozzle and a spray tube, wherein the spray nozzle comprises an anterior and a posterior, with the anterior of the spray nozzle connects to the spray tube and the posterior of the spray nozzle connects the chamber back-side, wherein the spray nozzle comprises an interior contour and the interior contour includes a diverging part and a converging part; and a material delivery system connected to a top part of the pressurized chamber, wherein the material delivery system comprises a particle loading mechanism wherein a plurality of micro-particles is placed, the control device is connected to the material delivery system to control a release of the micro-particles, allowing the micro-particles to spray out from the sprayer due to a high speed gas in the pressurized chamber.

11. The low pressure-accelerated particle gene gun of claim 10, wherein the micro-particles are in a suspension or dry powdery micro-particles.

12. The low pressure-accelerated particle gene gun of claim 10, wherein the spray tube is a diverging straight tube.

13. The low pressure-accelerated particle gene gun of claim 10, wherein the spray nozzle further comprises a spray neck positioned in between the diverging part and the converging part, and a range of the interior contour of the converging part includes: $r_t<R_t<2r_t$, wherein $R_t$ represents a curvature radius of the converging part, $r_t$ is a radius of the spray neck.

14. The low pressure-accelerated particle gene gun of claim 10, wherein a range of the interior contour of the converging part includes: $\ominus<15$ degrees, wherein $\ominus$ is an angle between the diverging part and the center axis.

15. The low pressure-accelerated particle gene gun of claim 10, wherein the micro-particles comprise a plurality of nucleic acid-coated tungsten particles.

16. The low pressure-accelerated particle gene gun of claim 10, wherein the micro-particles comprise a plurality of nucleic acid-coated gold particles.

17. The low pressure-accelerated particle gene gun of claim 10, wherein the gas includes a nitrogen gas.

18. A gene transformation method using a gene gun, comprising:

providing a gene gun, wherein the gene gun comprises at least a pressurized chamber, a sprayer, a controlling device and a material delivery system;

placing a plurality of micro-particles in the material delivery system, wherein the micro- particles are in a suspension or a dry powdery form;

starting the gene gun; providing a gas to the pressurized chamber, the gas flows into the pressurized through the controlling device until a preset pressure is reached in the pressurized chamber;

discharging the micro-particles and accelerating the micro-particles by the gas in the pressurized chamber;

spraying out the micro-particles from the sprayer, wherein the sprayer comprises a spray nozzle and a spray tube, the spray nozzle comprises a converging part and a diverging part, and the spray tube comprises a diverging straight tube, wherein the gas is sprayed out of the spray nozzle at supersonic speed.

19. The method of claim 18, wherein the micro-particles comprise a plurality of nucleic acid-coated tungsten particles.

20. The method of claim 18, wherein the micro-particles comprise a plurality of nucleic acid-coated gold particles.

21. The method of claim 18, wherein a pressure at an exit of the sprayer is less than 1 atmospheric pressure.

22. The method of claim 18, wherein the gas is a nitrogen gas or a helium gas.

* * * * *